United States Patent [19]

Dyer

[11] Patent Number: 4,863,813
[45] Date of Patent: Sep. 5, 1989

[54] PRIMARY SOURCE OF ELECTRICAL ENERGY USING A MIXTURE OF FUEL AND OXIDIZER

[75] Inventor: Christopher K. Dyer, Summit, N.J.

[73] Assignee: Bell Communications Research, Inc., Livingston, N.J.

[21] Appl. No.: 244,350

[22] Filed: Sep. 15, 1988

[51] Int. Cl.$^4$ ............................................. H01M 8/10
[52] U.S. Cl. ........................................ 429/33; 429/40; 429/192
[58] Field of Search ................... 429/30, 33, 191–193, 429/40, 41, 44

[56] References Cited

U.S. PATENT DOCUMENTS

| | | | |
|---|---|---|---|
| 3,368,922 | 2/1968 | Salyer | 429/33 |
| 4,537,840 | 8/1985 | Tsukui et al. | 429/33 |
| 4,539,276 | 9/1985 | Harbach | 429/33 X |

Primary Examiner—Anthony Skapars
Attorney, Agent, or Firm—James W. Falk; Allen N. Friedman

[57] ABSTRACT

A solid electrolyte fuel cell capable of operating with a mixture of an oxidizer and a fuel includes a permeable catalytic electrode and an impermeable catalytic electrode separated by an electron insulating, ion conducting, gas permeable solid electrolyte. The device produces charge flow in an external circuit when the permeable electrode is exposed to a mixture including an oxidizer and a fuel such as hydrogen, methane or methanol.

The solid electrolyte can be a hydrated aluminum oxide, primarily of the pseudoboehmite structure and either electrode can be Pt or Pd. The solid electrolyte can be produced by exposing a bulk aluminum surface or a deposited layer of aluminum to water or water vapor or by exposing an anodically oxidized layer of aluminum oxide to water vapor. The device is produced in thin film form and can be produced by techniques compatible with thin film device fabrication.

The magnitude and direction of the charge flow is dependent on the particular fuel, so that the device can serve as a species selective, gas sensor which does not require the external application of sensing power in order to produce a measurable voltage.

17 Claims, 2 Drawing Sheets

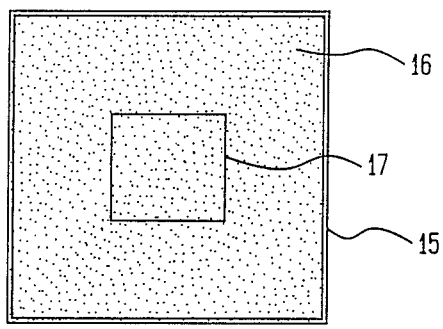
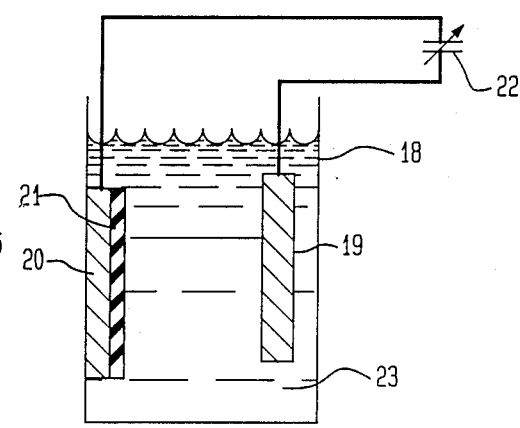
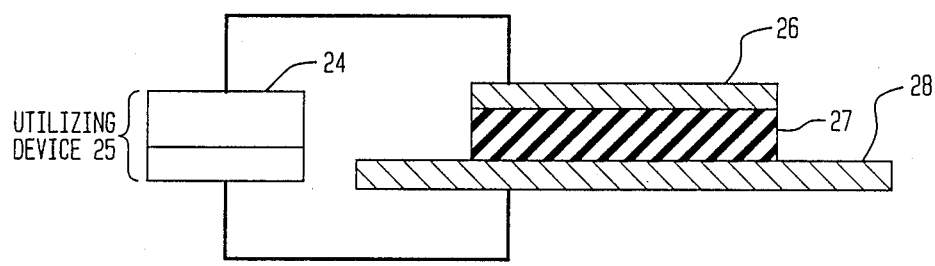
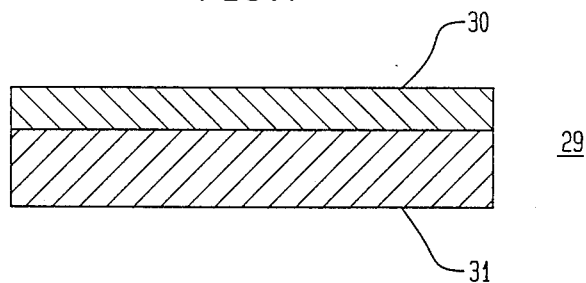

PRIMARY SOURCE OF ELECTRICAL ENERGY USING A MIXTURE OF FUEL AND OXIDIZER

BACKGROUND OF THE INVENTION

1. Field of the Invention

The invention is in the field of devices which consume gaseous or liquid fuels and produce electrical energy.

2. Description of the Prior Art

Many solid materials which are electrically insulating but permit the movement of certain ions are known in the art and are referred to as solid electrolytes. For example, it is known that at elevated temperatures beta-alumina is usefully conductive to some alkali metal ions. Such materials have been incorporated in devices which produce or store electrical energy.

Devices which produce electrical energy while producing oxidation and reduction reactions in substances which can be referred to as fuels and oxidizers are known in the art as fuel cells. In these prior art fuel cells the substance being oxidized and the substance being reduced are separated by a material which does not permit the flow of electrons, but does permit the flow of ions produced in the oxidation-reduction reaction. In addition, it is desirable to have the separating material as impermeable as possible to the oxidizing substance and the fuel substance. Fuel cells which consume hydrogen or hydrogen containing gases and oxygen are known in the art. Fuel cells consuming carbon monoxide are also known. ("Fuels Cells: Their Electrochemistry", J. O'M. Bockris and S. Srinivasan, McGraw Hill, 1969). These cells typically utilize liquid electrolytes to separate the gases.

SUMMARY OF THE INVENTION

I have found that devices can be produced that are primary sources of electrical energy when a permeable electrode is exposed to a mixture of an oxidizer and a fuel containing the chemical species hydrogen. These devices include one electrode that is permeable to the gases of the mixture and one electrode that is impermeable to the gases of the mixture. The electrodes are separated by a solid electrolyte that is permeable to the oxidizer, the fuel and the products of the reaction between them, is electron insulating, and is ionically conductive particularly to hydrogen ions (protons). Both electrodes are catalytic to the oxidation and reduction reactions. Fuel cells in which the permeable electrode was exposed to a mixture of gases have been produced. In addition, species sensitive gas detectors have been produced with the same general structure. The solid electrolyte can be, for example, a hydrated aluminum oxide found to possess a useful degree of reactant permeability and hydrogen ion conductivity or a polymeric material possessing a useful degree of reactant permeability and hydrogen ion conductivity. The permeability to the reactants must be sufficient to sustain oxidation and reduction reactions at the separated electrodes.

The ability to supply both the fuel and the oxidizer from one side of the cell is of particular advantage in planar technologies such as semiconductor integrated circuits. The ability to use unseparated gases to generate electrical energy could be an advantage in more general fuel cell applications. A gas sensor which generates its own electrical energy is of particular advantage in not requiring the continuous application of externally generated power.

Thin layers of hydrated aluminum oxide are known in the art to be producible by several methods ("Oxides and Oxide Films", R. S. Alwitt, Ed. by J. W. Diggle and N. K. Vijh, Vol. 4, Marcer Dekker, N.Y. 1976, pp. 169-253). These include first producing a layer of aluminum oxide, for example by anodic oxidation of aluminum, and then exposing the oxide layer to water or water vapor. Also known is the direct exposure of a metallic aluminum to water or water vapor. The crystalline form and composition of the hydrated layer are dependent upon the conditions of the hydration. Under one range of conditions described in the Alwitt reference, pseudoboehmite is produced. Pseudoboehmite layers produced by exposing aluminum to water are used during the production of capacitors as a precursor to anodic oxidation of the capacitor plates in order to increase the crystallinity of alumina dielectric films. (1) R. S. Alwitt—see reference above, (2) C. K. Dyer and R. S. Alwitt, Electrochimica Acta, Vol. 23, 1978, pp. 347-354. The increased crystallinity of the dielectric films is known to improve the physical and dielectric properties of the anodically produced barrier layer.

Many devices are known in the art to detect the presence of gases. Those that are electronic in nature, characteristically require the imposition of a bias voltage or the flow of a sensing current generated by an external circuit.

The form of hydrated aluminum oxide which I have found to be most advantageous for these devices is pseudoboehmite. As it possesses the highest degree of hydrogen ion conductivity, it also is sufficiently permeable to the gases necessary for fuel cell and gas detector devices. Other forms of hydrated aluminum oxide can form all or part of the electrolyte for those uses (e.g. gas detecting) in which minimization of the series resistance of the device is not a controlling consideration. One advantage of the aluminum-oxygen-hydrogen system is that it does not require the use of a sealed container when operating below explosive mixtures of reactant gases.

Pseudoboehmite and other forms of hydrated aluminum oxide can be produced by methods compatible with thin film device processing techniques (e.g., semiconductor devices). This makes possible the integration of power sources in close proximity to the circuitry being powered. Powering circuitry in this manner would only require the provision of an enclosure or hood to guide, for example, the mixture of oxidizing gas and fuel gas to one surface of the cell. The permeability to the mixed gases of the electrode at that surface can be due to the metal having a thin loose structure (e.g., as produced by sputtering) or by being patterned with an array of apertures. It is advantageous that both the permeable electrode and the impermeable electrode be of metals or alloys that catalyze the oxidation and reduction reactions that produce the charge flow in the external circuit. For example, fuel cells using mixtures of hydrogen or methane or methanol with oxygen (possibly together with other gases that do not take part in the reactions) have been fabricated using platinum or palladium electrodes. It was observed that when methanol vapor was used as a fuel gas, the polarity of the cell was opposite to the polarity of the cell with hydrogen or methane as the fuel gas. Thus, the fuel cell can be optimized to serve as a species selective detector of the presence of the fuel gas. Generally, the use of thicker electrolyte layers would tend to increase the species selectivity, while the attendant increase in series resistance of the cell would not be detrimental to that use.

BRIEF DESCRIPTION OF THE DRAWING

FIG. 4 is an elevational view in section of a chamber within which the solid electrolyte is being formed by exposing a body of aluminum to $H_2O$ vapor.

FIG. 5 is an elevational view in section, partly schematic, of a container in which an aluminum body is being anodically coated with aluminum oxide.

FIG. 6 is an elevational view in section, partly schematic, of an exemplary gas sensor.

FIG. 7 is an elevational view in section of a composite impermeable electrode.

DETAILED DESCRIPTION

Fuel Cells

Figure 1:
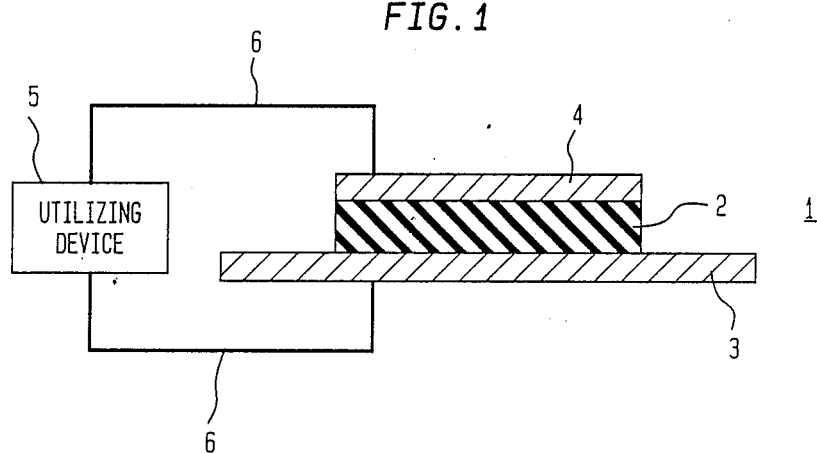
FIG. 1 is an elevational view in section, partly schematic, of an exemplary source of electrical current.

Fuel cells of the invention are illustrated in FIG. 1 which shows a fuel cell 1 including a solid electrolyte 2, an impermeable electrode 3, and a permeable electrode 4. The electrodes are connected to a utilizing device 5 by means of electrical conductors 6.

Further consideration in the design in the fuel cells is the series electrical resistance of the device. This depends in principal part on the composition and thickness of the solid electrolyte. Making the electrolyte layer thinner reduces the series electrical resistance of the cell; however, this also serves to reduce the concentration difference between the fuel and oxidizer mixtures at the different electrodes due to differential fuel and oxidizer diffusion. This reduction in concentration difference reduces the voltage output of the cell. For thinner cells, the effects of "gettering" of one of the consumable components becomes more important in producing the required concentration difference. In a series of fuel cells constructed with platinum electrodes or palladium electrodes and with the conditions of producing the solid electrolyte in the range in which pseudoboehmite is the predominant constituent, fuel cells powered by a mixture of hydrogen and oxygen gas were observed to produce cell voltages in the region of one half to one volt with current outputs in the region of three milliamperes per square centimeter. In these cells, the impermeable electrode was positively charged with respect to the permeable electrode showing that the impermeable electrode was oxygen rich with respect to the permeable electrode. Here the effect of "gettering" of hydrogen at the permeable platinum or palladium electrode was the probable predominant mechanism in producing a lower concentration of hydrogen at the impermeable electrode.

Depending upon the composition and structrue of the hydrated aluminum oxide electrolyte, thicknesses from 30 Angstroms to 10 microns produce cell of usefully low series resistance.

Figure 2:
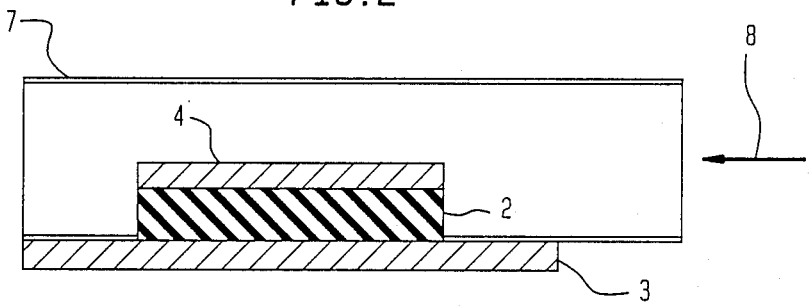
FIG. 2 is an elevational view in section of an exemplary source of electrical current including means for directing the fuel and oxidizer to the permeable electrode.

FIG. 2 shows a gas or liquid stream 8 containing mixed fuel and oxidizer being confined to the vicinity of a fuel cell by a hood 7. In systems producing water, hydrogen and oxygen can be regenerated by reversing the current through the cell.

The Electrolyte

The solid electrolytes 2 in devices made in accordance with my invention have a usefully high conductivity for hydrogen ions ($H^+$) or hydronium ions ($H_3O^+$). They are permeable to the fuel, the oxidizer and the product of the reaction between them. In addition, they preferably should be electron insulators with a resistivity of at least $10^6$ ohm-centimeters. In the preferred embodiments they are also capable of being made in very thin layers, often below one micron in thickness. In accordance with the invention, two classes of solid electrolyte materials may be utilized. One class consists of selected hydrated aluminum oxides. The other class consists of selected polymeric materials.

Figure 3:
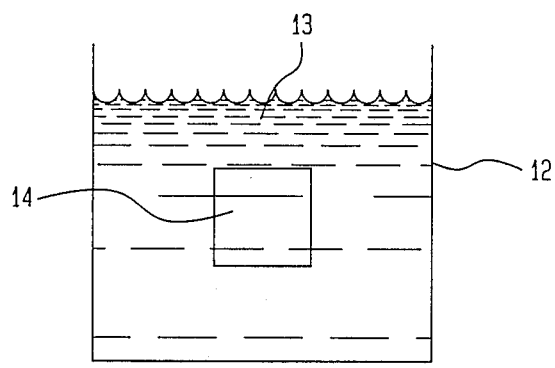
FIG. 3 is an elevational view in section of a container within which the solid electrolyte is being formed by exposing a body of aluminum to liquid $H_2O$.

The physical properties and conditions of formation of materials of the aluminum oxide-water system have been extensively studied. A review of many of these studies appears as Chapter 3 of "Oxides and Oxide Films", ed. by J. W. Diggle and A. K. Vijh (referred to above). Depending on the particular conditions, the product of the reaction between aluminum and water includes boehmite, pseudoboehmite, bayerite, gibbsite and combinations of these materials. One of these materials, pseudoboehmite has been found to have a particularly high conductivity for hydrogen ions or hydronium ions. Materials including at least 50% pseudoboehmite are to be preferred, materials including at least 95% pseudoboehmite being most preferred. Suitable gas permeable solid electrolyte films of the aluminum oxide-water system can be produced by several methods: The materials form on a clean metallic aluminum surface 14 exposed to water in liquid form 13 in a container 12 (See FIG. 3) or exposed to water in vapor 16 (See FIG. 4) form in a chamber 15 in a temperature range from 20° C. to 374° C. Pseudoboehmite is predominant in films produced in the temperature range from 90° C. to 100° C. Solid electrolyte films can also be produced by exposing aluminum oxide to water and/or liquid vapor phases. The pseudoboehmite form is predominant in layers produced in temperatures from 90° C. to 100° C. Aluminum oxide layers intended for this use can be produced by anodization of metallic aluminum. FIG. 5 shows an aluminum body 20 being anodized in a container 18 of an electrolyte bath 23 with the anodizing voltage being supplied by electrical source 22. Thicker layers can be produced by a multilayer process including alternate steps of aluminum deposition and exposure of the aluminum or anodized aluminum surface to water. RF backsputtering can be used during deposition of the metallic aluminum prior to water exposure. Such backsputtering can improve the uniformity of coverage of the aluminum and therefore of the permeable solid electrolyte film. The production of solid electrolyte films from anodically produced aluminum oxide films have the advantage that such anodically produced oxide films are characteristically of very uniform thickness and can be grown to precise thickness. In the multilayer process using sequential aluminum depositions prior to the hydro-thermal treatments, solid electrolyte films of approximately 500 nanometer thickness have been produced with 3 to 5 sequential processing steps.

Carbon based polymeric materials have been found which possess the required hydrogen ion conductivity and permeability to fuel, oxidizer and products of the reaction between them. Polyacrylic acid is an example of the hydrated or hydroxylated polymers in which ionic hydrogen species can be readily mobilized. This supplies the necessary hydrogen ion mobility. Polymers commonly have sufficient gas permeability and electronic resistance to be useful as solid electrolytes of the invention.

The devices of the invention depend for their operation on their ability to create a different oxidizer and fuel species mixture at the unexposed electrode. This is achieved by species-selective reaction kinetics at the exposed electrode and differences in the diffusion properties of the reactants through the gas-permeable electrolyte. The electrochemical half cell reactions will only produce usable electrical current in the external circuit if there is a sufficiently different concentration of oxidizer and fuel at the two electrodes.

Fuels and Oxidizers

The fuels which are consumed by devices of the invention in order to produce electrical energy are hydrogen-containing liquid or gaseous material such as hydrogen, methane and methanol. The fuels can be in liquid or gaseous form. Often when the fuel is supplied to the system in gaseous form, it may reach the surface of the exposed electrode through an adsorbed liquid layer. While many oxidizer, such as the halogens are known, the most common oxidizer is gaseous oxygen. However, the invention also contemplates the use of solutions of fuel and oxidizer species. For example, since blood is an oxygenated liquid which includes hydrogen-containing fuels such as sugars, one can contemplate a device of the invention exposed to a supply of flowing oxygenated blood producing electricity to power devices such as pacemakers. Another contemplated use for devices of the invention is the powering of semiconductor integrated circuitry from fuel cells incorporated in an integral manner with the semiconductor devices and exposed to a mixture of fuel and oxidizer gases. There are many other situations in which the use of unseparated gases is either convenient or inexpensive. For example, a mixture of methane gas and air is present over garbage dumps. Such mixtures have been utilized to produce electrical energy by the combustion powering of a heat engine driving a generator. However, the devices of the invention could be used to produce electricity directly from the methane-air mixture.

The Electrode

Both the permeable 4 and the impermeable 3 electrodes (See FIG. 1) must be catalytic to the half cell reaction which produces at one electrode a surplus supply of electrons which will flow in the outer circuit and positive ions which are conducted through the solid electrolyte. At the other electrode the electrode material must be catalytic to the reaction consuming the surplus electrons and neutralizing excess positive ionic charge in the electrolyte by, for example, generating negative ions. A large number of metallic materials are known to be catalytic to such reactions. Of particular interest are materials such as platinum, palladium, gold, nickel or various alloys including these materials. Non-metals such as electronically conducting mixed oxides with spinel or perovskite structure could serve as either or both electrodes. One property of many of these materials which enhances the operation of devices of the inventions is the kinetic differentiation between the fuels and the oxidizer in the fundamental rate of oxidation and reduction respectively. This "gettering" effect can change the concentration of fuel and oxidizer in the permeable electrolyte so that a sufficient difference in the fuel and oxidizer mixture at the two electrodes produces a useful voltage difference between the two electrodes. In exemplary devices voltage difference of up to one volt have been observed.

The electrode that is exposed to the mixtrue of fuel and oxidizer materials must permit these materials to pass into the solid electrolyte. This effect can be described as permeability. The provision of a permeable electrode can be accomplished in many ways. Thin layers of electrode material produced, for example, by sputtering are sufficiently porous in thicknesses up to approximately 100 nanometers, depending on the surface topography. Electrode layers which permit the passage of fuels and oxidizers can be produced using thicker layers of electrode material and producing a pattern of apertures in the material which permit the flow of the fuel and oxidizer materials to the surface of the solid electrolyte. In this situation, the minor diameter of the apertures is preferably of the order of the thickness of the solid electrolyte layer. As shown in FIG. 7, the impermeable electrode may be a composite structure 29 including a layer 30 of the catalytic material, which may itself be permeable, on a substrate 31 which is itself impermeable to the reactants. In the device structure the catalytic material 30 is in contact with the solid electrolyte.

EXAMPLES

Following are specific examples of fuel cells of the invention:

EXAMPLE 1

A fuel cell is produced by first sputtering a layer of platinum of approximately 50 nanometers (nm) thickness on a quartz substrate. Following the platinum sputtering, a layer of aluminum approximately 30 nm thick is sputtered on the platinum surface. The assembly is then exposed to deionized boiling water until the layer of Al becomes transparent indicating conversion to pseudoboehmite is complete. The sequence of sputtering a thin Al film onto the pseudoboehmite film then hydrothermally converting it to pseudoboehmite is repeated up to five times when only thin layers of Al are used in order to cover pinholes and other imperfections in film coverage. This produces pseudoboehmite layers totaling approximately 500 nm in thickness. For a thick layer of Al on Pt, one sequence suffices.

A thin film of Pt is sputtered onto the top surface of the pseudoboehmite, of sufficient thickness to allow for electrical continuity but not too thick, since gases must permeate the top Pt layer. There is no fuel cell action for a very thick impermeable top layer of Pt, i.e., exposure to a mixture of oxygen and hydrogen produces no voltage between the top and bottom electrodes. Masking of the top and bottom Pt electrodes allowed a substantial area of overlap of the two electrodes separated by pseudoboehmite as well as small regions of no overlap where electrical connection could be made mechanically without risk of short circuiting the device.

The device was tested in a stainless steel pressure vessel fitted with electrical feedthroughs and pressure-monitoring devices. Electrical current and voltage were generated in various mixtures of hydrogen and oxygen (or air) over the entire range of total pressures available with the pressure vessel (0.01 psia to 50 psia). Gas compositions from less than 1% oxygen to more than 99% oxygen in hydrogen made the fuel cell active, delivering currents of up to 3 mA/cm$^2$ at up to 0.95 volts. A typical stable running condition over several hours was approximately 1 mA/cm$^2$ at approximately 0.6 volt. Inefficiencies in producing electrical energy arise due to the direct chemical combination of the constituents of the gas mixture on the top Pt electrode. Efficiency was raised from 5% to >50% by operating in humid conditions at low total pressure e.g., in a mixture of $H_2$ at 2 psia and $O_2$ at 1 psia together with water vapoor to give a total of 3.5 psia. In such a mixture, the fuel cell gave a lower current of 0.2 mA/cm$^2$ for over one hour for an efficiency of 52%.

EXAMPLE 2

Other electrode materials have been used to make the fuel cell. Using the same procedure as in Example 1 but with both top and bottom electrodes made by sputtering Pd, lower voltages were generated in mixed fuel + oxidizer gases e.g., 0.3 V at ~4 $\mu$A/cm~4 $\mu$ in air with 6 psia $H_2$ (total pressure approximately 20 psia). Using a Pt bottom electrode and a Pd top electrode, higher voltages and currents were measured e.g., 0.8 V at 0.1 mA/cm$^2$ in a mixture of 2 psia $H_2$ plus 1 psia $O_2$. Use of a Ni top electrode with a Pt bottom electrode provided an opposite polarity to the fuel cell. The top Ni electrode was electrically positive towards the bottom Pt electrode (which is otherwise positive for a Pd or Pt top electrode) in an $O_2+H_2$ mixture, e.g., a current density of approximately 20 $\mu$A/cm$^2$ at approximately 350 mV was recorded in air with 6 psia $H_2$ added (total pressure approximately 20 psia).

EXAMPLE 3

Different fuels were used with a Pt/pseudoboehmite/Pt fuel cell similar to that described in Example 1. Using a mixture of methane (14.4 psia) plus oxygen (5.6 psia) a voltage of 100 mV (bottom Pt electrode positive) was developed for 10 $\mu$A/cm$^2$. Efficiency of elecrtrical conversion of the methane was very high (apparently 100%) since no pressure drop in the testing vessel was detected after 2 hours.

Using methanol vapor in air (total pressure=atmospheric pressure) the polarity of the fuel cell was changed so that the top Pt electrode was approximately 300 mV positive to the bottom Pt electrode while the fuel cell yielded a current of 25 $\mu$A/cm$^2$. The efficiency of conversion of the fuel cell using methanol as the fuel mixed with air was approximately 4%.

EXAMPLE 4

A fuel cell made by the procedure in Example 1 was built onto a silicon wafer after an insulating layer of $Al_2O_3$ was sputtered onto the top of the poorly conducting polished surface. Performance was similar to the fuel cell described in Example 1.

Gas Detectors

A surprising experimental result suggests a different use for devices of similar structure to the fuel cells described above. When such cells were exposed to a mixture of air and methanol vapor, the cell produced the opposite polarity as it did when exposed to a mixture of hydrogen (or methane) and air. This suggests the use of such devices as species sensitive gas detectors. The optimization of the design of such devices for use as gas detectors places different constraints upon the structure of the device than were placed on the structure by the requirements for fuel cell usage. For example, the use as a gas detector does not require as low a series resistance as is required for the fuel cell use. Layers as thick as 1 millimeter could be useful. The ability to use thicker layers of solid electrolyte also serves to enhance the sensitivity of the detector because it increases the concentration difference of the fuel and oxidizer mixture at the permeable and the impermeable electrodes. Such gas detectors of the invention have the advantage that they are self-powered and do not require the maintenance of sensing power from an external circuit. FIG. 6 shows an exemplary gas sensor of the invention including a permeable electrode 26, a solid electrolyte 27 and an impermeable electrode 28. In this Figure, the utilizing device 25 includes a means 24 for differentiating between the presence or absence of a flow of electrons and the direction of the electron flow.

EXAMPLE 5

A sensor consisting of a Pt bottom electrode (obtained by sputtering Pt) covered by a 0.5 $\mu$m thick layer of pseudoboehmite and a thin gas permeable Pt top electrode gave the following voltages and currents:

(1) approximately 1% psia $H_2$ in air:+0.9 V (open circuit voltage) and an initial current of minus 200 $\mu$A/cm$^2$ and +0.5 V on connecting to a resistive load of approximately 500 ohms.

(2) approximately 1% methanol in air : minus 0.3 V and an initial current of +25 $\mu$A/cm$^2$ on connecting to approximately 500 ohms resistive load.

What is claimed:

1. A device which is a source of electrical current comprising a first electrode and a second electrode separated by and in contact with a solid electrolyte body characterized in that the first electrode is permeable to an oxidizer and a fuel, the second electrode is impermeable to the oxidizer and the fuel and the solid electrolyte body consists essentially of an electron insulating material which is also ionically conducting to at least a first ionic species and which material is permeable to the oxidizer, the fuel and products of the electrochemical reactions of the oxidizer and the fuel.

2. A device of claim 1 in which the said species is ionic hydrogen.

3. A device of claim 1 including means for exposing the first electrode to a mixture comprising the oxidizer and the fuel.

4. A device of claim 1 in which the oxidizer and fuel are gaseous.

5. A device of claim 1 in which the said material consists essentially of a hydrated oxide of aluminum consisting primarily of the pseudoboehmite structure.

6. A device of claim 5 in which the said material is at least 50% of the pseudoboehmite structure.

7. A device of claim 5 in which the solid electrolyte body is from 30 Angstroms to 10 microns in thickness.

8. A device of claim 1 in which the said material consists essentially of a crabon based polymer.

9. A device of claim 8 in which the carbon based polymer is polyacrylic acid.

10. A device of claim 1 in which the oxidizing gas is oxygen and the fuel is at least one member of the group consisting of hydrogen, methane and methanol.

11. A device of claim 1 including means for electrically connecting the first electrode and the second electrode to a utilizing device.

12. A device of claim 10 in which the solid electrolyte body is form 30 Angstroms to 1 millimeter in thickness.

13. A device of claim 12 in which the utilizing device includes means for differentiating between the presence or absence of a flow of electrons and the direction of the flow of electrons.

14. A device of claim 1 in which the said material is produced by a method including exposing a metallic aluminum body to $H_2O$.

15. A device of claim 14 in which the temperature of the aluminum during the exposure is at least 20° C.

16. A device of claim 2 in which the first electrode and the second electrode consist essentially of Pt or Pd or alloys of Pt and Pd.

17. A device of claim 1 in which the said material is produced by a method including the steps of anodizing a metallic aluminum body to produce an aluminum oxide film and subsequently exposing the aluminum oxide film to $H_2O$.

* * * * *